United States Patent [19]

Feldman

[11] Patent Number: 5,445,958
[45] Date of Patent: Aug. 29, 1995

[54] PROCESS FOR PURIFYING BLOOD CLOTTING FACTORS

[75] Inventor: Peter A. Feldman, Oxford, England

[73] Assignee: National Blood Authority, Hertfordshire, England

[21] Appl. No.: 24,113

[22] Filed: Feb. 23, 1993

Related U.S. Application Data

[63] Continuation of Ser. No. 476,454, Jul. 20, 1990, abandoned.

[30] Foreign Application Priority Data

Dec. 22, 1987 [GB] United Kingdom ................. 8729822

[51] Int. Cl.6 .................... C12N 9/74; C07K 14/745; C07K 1/18
[52] U.S. Cl. .................... 435/214; 530/381; 530/384; 530/382; 530/383; 530/412; 530/416
[58] Field of Search ............... 530/381, 384, 382, 412, 530/411, 416; 435/214

[56] References Cited

U.S. PATENT DOCUMENTS 4,473,553  9/1984  Zuffi et al. ...................... 530/381
4,637,932  1/1987  Parcham ......................... 530/381

OTHER PUBLICATIONS

Scopes, R. K. 1987. in: *Protein Purification. Principles and Practice*. Second Edition. Springer-Verlage. New York, pp. 184–185.
Weerasinghe et al. (1985). BBA 839:57.
Andersson et al. (1975). Thrombosis Res. 7:451.
Wilson et al. (3rd ed.). Arnold, p. 234.
Pharmacia. (1986). Affinity Chromatography: Principles and Methods p. 32.
Pinley et al. (1986). Thrombosis Res. 41:89.
Weerasinghe et al. (1985) Biochim. Biophys. Acta 839:57–61.
Porath, J. et al., *Nature*, 258:598–9 (1975) "Metal chelate affinity chromatography, a new approach to protein fractionation".
Porath, J. et al., *Arch.Biochem. Biophys.*, 225:543–7 (1983) "Immobilized metal affinity chromatography of serum proteins on gel-immobilized group III A Metal ions".
Porath, J. and Olin, B., *Biochemistry*, 22:1621–1630 (1983) "Immobilized metal ion affinity adsorption and immobilized metal ion affinity chromatography of biomaterials".
Fanou-Ayi L. and Vijayalakshmi M., *Ann. N.Y. Acad. Sci.*, 413:300–306 (1983) "Metal Chelate affinity chromatography as a separation tool".
Andersson, L., *J. Chromatog.*, 315:167–174 (1984) "Fractionation of human serum proteins by immobilised metal affinity chromatography".
Andersson, L.-O., *J. Chromatog.*, 215:153–164 (1981) "Purification and studies of components of the haemostatic system by affinity chromatography".
Liebman, H. A., et al., *PNAS*, 82:3879–3883 (1985) "Immunoaffinity purification of factor IX (Christmas factor) by using confomation specific antibodies directed against the factor IX—metal complex".
Hashimoto, N., et al., *J. Biochem.*, 97:1347–1355 (1985) "A method for systematic purification from bovine plasma of six vitamin-K-dependent coagulation factors: Prothrombin factor X, factor IX, protein S, protein C and protein Z".

*Primary Examiner*—Christopher S. Low
*Attorney, Agent, or Firm*—Burns, Doane, Swecker & Mathis

[57] ABSTRACT

A method for at least partially separating vitamin K-dependent blood clotting factors from a mixture containing at least one such factor, e.g. a prothrombin complex concentrate, which comprises adsorption of said mixture on to a chelate of a polyvalent metal immobilized on an inert support, e.g. $Cu^{2+}$-primed Chelating Sepharose, followed by elution to yield one or more fractions enriched in respect of one of said factors.

20 Claims, No Drawings

PROCESS FOR PURIFYING BLOOD CLOTTING FACTORS

This application is a continuation of application Ser. No. 07/476,454, filed Jul. 20, 1990 now abandoned.

This invention concerns an improved method for the purification or enrichment of vitamin K-dependent blood clotting factors in fractions containing such factors.

Plasma obtained from blood of human or animal origin contains a number of valuable physiologically active substances, notably the various blood clotting factors, some of which are used in medicine for the treatment of individuals lacking one or more of such substances. The blood clotting factors, i.e. the members of the so-called blood clotting cascade, comprise a group of inactive and active proteolytic enzymes and modified proteins related in the following manner:

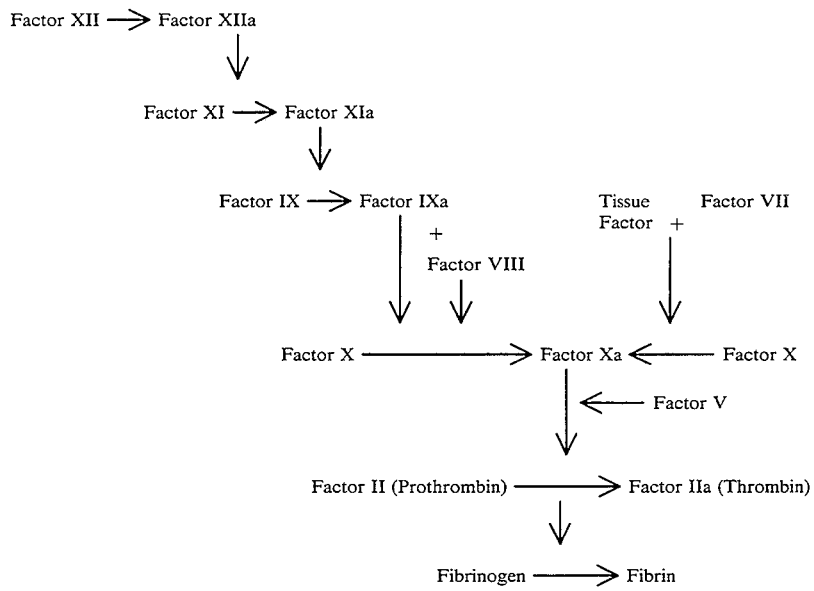

The subscript "a" means that the enzyme is in the activated form.

Further significant plasma proteins, which may be considered to fall within the general category of blood clotting factors, include Protein C and Protein S. Protein C is an inactive zymogen of the proteolytic enzyme Activated Protein C (APC,$PC_a$). Unlike the above-mentioned clotting factors, APC has an anticoagulant effect which functions through the proteolysis of Factor V and Factor VIII which are thus inactivated. Activation of Protein C appears to be by a feedback process involving thrombin and an endothelial-bound protein, thrombomodulin, which both function during the coagulation process. The activity of APC is then enhanced by the presence of Protein S, which seems to act as a cofactor.

A number of the above factors, namely II, VII, IX, X, and also Protein C and Protein S, have been shown to be vitamin K-dependent. These factors, both in the active and inactive form (apart from activated Factor II), carry terminal gamma-carboxy glutamic acid residues which are introduced by an enzymic process mediated by vitamin K. Additionally, Protein C, Protein S and Factors X and IX, but not prothrombin (Factor II), have been found to possess a modified aspartic acid residue, namely a $\beta$-hydroxyaspartic acid residue.

Thus, the vitamin K-dependent blood clotting factors represent a group of related acidic proteins having closely similar physicochemical properties. The acidic nature of these substances has enabled them previously to be isolated as a group though their structural and chemical similarities have made it difficult to separate the individual proteins using conventional techniques such as anion exchange chromatography.

Apart from Factor VIII, which is not part of the prothrombin complex, the most frequently administered blood clotting factor is Factor IX. Traditionally, Factor IX has been provided as a concentrate of all the factors of the prothrombin complex, II, VII, IX and X, although Factor VII is sometimes provided separately from IX, II and X.

Following infusions of such Factor IX concentrates, there have been a few reported cases of venous thrombosis and disseminated intravascular coagulation (DIC). These undesirable responses might be ascribed to a hypercoagulable state encouraged by high levels of unnecessary clotting factors infused with the Factor IX and/or by unwanted thrombogenic components in the concentrate. Intense and lengthy administration of Factor IX may lead to much higher than normal levels of Factor II, which is infused in the equivalent amounts and has a longer half-disappearance time in plasma. Some hypotheses based on in vitro studies or animal models have also suggested that a combination of factors might be more thrombogenic than Factor IX alone. Indeed, present dosage levels of Factor IX are in part limited by the need to avoid excessive levels of Factor II.

Furthermore, following treatment with factor VIII concentrates, some haemophilia A patients show signs of non-viral immunosuppression. A similar immunosuppression in haemophilia B patients after treatment with Factor IX concentrate suggests that the response in both cases may be due to an unwanted contaminant in the concentrates.

Donor plasma pools from which clotting factor concentrates are prepared contain the causative agent (probably viral) of non-A non-B hepatitis and must be assumed to carry the risk of contamination with viruses (e.g. hepatitis B and HIV). To improve product safety, the concentrates must undergo virucidal treatments, which may be complicated by the presence of contaminant proteins. For example, this virucidal treatment may be easier to devise in a more highly purified concentrate in which interference from unnecessary proteins can be minimised.

In general, it is preferable in principle to administer a blood clotting factor intended to replace or supplement a specific clotting factor in a human patient, without simultaneously raising the level of other factors or, indeed, any contaminants which might produce unwanted physiological effects.

There is thus a need for an improved method of at least partially separating the vitamin K-dependent clotting factors in order to reduce or even eliminate some of the above problems. It has now been found that the vitamin K-dependent blood clotting factors can be at least partially separated from each other by metal chelate chromatography.

According to the present invention, there is provided a method for at least partially separating vitamin K-dependent blood clotting factors from a mixture containing at least one such factor, characterised in that said mixture is adsorbed on to a chelate of a polyvalent metal immobilised on an inert support, followed by elution to yield one or more fractions enriched in respect of one of said factors.

In general said mixture will contain at least two vitamin K-dependent blood clotting factors. Thus, although the invention includes purification or enrichment of fully functionalised clotting factors. derived from microbiological cultures using recombinant DNA technology, the source of the clotting factors will commonly be blood plasma, particularly human plasma.

The mixture of factors to be treated in accordance with the invention will most commonly be a plasma fraction concentrate from which some plasma factors have already been removed.

In obtaining the mixed factors from plasma, typical initial fractions containing the desired components include cryoprecipitate supernatant the supernatant remaining after cryoprecipitation of Factor VIII concentrate), Fraction I supernatant and fractions obtained after adsorption of the plasma with various affinity reagents, e.g. heparin Sepharose. In general, the factors will have been further concentrated by adsorption on to an anion exchange resin such as diethylaminoethyl (DEAE) cellulose, DEAE Sephadex or DEAE Sepharose to produce a prothrombin complex concentrate.

It should be noted that under optimal conditions for Factor IX preparation, DEAE cellulose does not bind Factor VII, although higher capacity ion-exchangers (e.g. DEAE Sephadex and DEAE Sepharose) bind Factor VII more efficiently under accepted industrial processing conditions. Thus the prothrombin complex concentrate from DEAE cellulose will not contain Factor VII. This difference in behaviour enables a concentrate containing predominantly Factor VII to be obtained, although this can also benefit from purification and enrichment according to the invention. While the anion exchange resin concentrates may beneficially be treated in accordance with the invention, other combinations of the factors may also advantageously be treated to enhance the concentration of a desired factor.

In particular, an enriched fraction produced in accordance with the invention, which may contain only two of the factors, may be subjected to a second treatment to produce still further enrichment.

Existing purification systems have several inherent disadvantages. Heparin-Sepharose gives poor resolution and clotting factor activities when used on an industrial scale. Sulphated dextran produces Factor IX with a very short NAPTT (see below) which could lead to thrombotic episodes in clinical usage and dextran sulphate is cytotoxic and any leakage from such an affinity matrix may seriously contaminate the product. The present treatment has advantages over such purification systems in all these respects.

While some benefit can be obtained by a batchwise treatment of the initial mixture with the immobilised metal chelate followed by simple washing to remove the most readily eluted factor (s), the most preferred mode of operation is column chromatography. The mixture of factors can thus be applied to the top of the column and an eluant run through to provide fractions containing the separated and partially separated factors. Alternatively, the initial mixture can be applied batchwise to the immobilised metal chelate prior to loading the column.

The chelated polyvalent metals for use in the process of the invention are generally in the divalent state, $Cu^{2+}$ being particularly preferred.

The immobilised chelating agent may comprise a conventional backbone or skeletal support (such as a support based on cellulose, polystyrene, acrylamide, silica, fluorocarbons, cross-linked dextran or cross-linked agarose) carrying groups capable of chelating polyvalent metals. Such groups are well known and can be found in text books such as Martell and Calvin, Chemistry of the Metal Chelate Compounds, Prentice Hall, Inc. New York (1952).

Iminodiacetic acid groups, $-N(CH_2COOH)_2$, are particularly preferred chelating groups.

The chelating groups will generally be spaced from the backbone or skeleton of the support by linear "spacer" groupings such as optionally substituted hydrocarbon or carbohydrate chains, having advantageously from 8 to 16 atoms, e.g. about 12 atoms, between the chelating group and the support. Such spacer groupings may be introduced into appropriate substrates by reaction with a divalent reagent of desired chain length. The preferred metal binding matrix is Chelating Sepharose which is a beaded 6% agarose product sold by Pharmacia AB which carries iminodiacetic acid groups, linked to the sepharose by a chain:

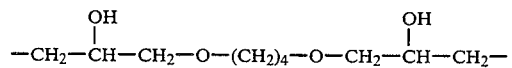

The binding of proteins to the chelating support is dependent on at least four considerations;
(i) ionic strength, where increased ionic strength apparently minimises non-specific binding;
(ii) the presence of buffer ions both in the sample to be loaded and in the equilibrated metal-chelate gel;
(iii) loading capacity of the matrix: this is a finite quantity which can be fully saturated by the more tightly binding proteins at the expense of the weaker binding proteins. The capacity of the matrix for a particular protein is thus dependent on the composition and the concentration of the protein mixture with which it is challenged during loading and the adsorption contact time;

(iv) with both binding and elution, pH is a recognised effector.

It has been found that at relatively high ionic strengths, the binding to the chelate of prothrombin (Factor II) and thrombin is reduced, while that of Factors IX and X and Protein C is increased. Since, in general, it is desirable to reduce the prothrombin level in concentrates of the other blood clotting factors, in order to avoid the possibility of thrombin formation, this finding is particularly useful. It is thus preferred to load the metal chelate in an aqueous solution of relatively high ionic strength, for example containing 0.4 to 1.0M, preferably 0.4 to 0.6M, most preferably about 0.5M, sodium chloride and/or one or more other electrolytes providing a solution of equivalent ionic strength.

Different vitamin K-dependent clotting factors have different pH optimal for binding to a chelating gel and consequently selection of the pH of the loading buffer solution provides further means for promoting preferential binding to the chelating gel of one or more vitamin K-dependent clotting factors over another such factor. Thus, for example, in the case of $Cu^{2+}$-primed Chelating Sepharose, optimum binding of Factors II, IX and X occurs at pH 6.0–7.0, above pH 7.0 and pH 6.5–7.5 respectively. Consequently, for example, to enhance differential binding to such a gel of Factor IX over prothrombin, the loading pH will desirably be pH 7.0 or above.

Further, where it is desired to deplete prothrombin from one or more other vitamin K-dependent clotting factors, decreased binding of prothrombin in favour of other blood clotting factors, e.g. Factor IX, may be promoted by appropriate selection of the adsorption contact time and the loading challenge. Thus, for optimization of separation of Factor IX from Factor II on $Cu^{2+}$-primed Chelating Sepharose starting with a prothrombin complex concentrate, the adsorption contact time will advantageously be over 20 minutes, more preferably about 40 minutes or longer, and the loading challenge will desirably be such that a Factor IX loading of 100–450 F.IX:Ag units per ml. of gel is achieved.

Column chromatography is preferred. The initial mixture of factors is preferably applied to the top of a column, but it is also possible to load the initial mixture on to the immobilised chelate batchwise. After washings, mostly at high ionic strength, the remaining factors can be separated either by batch elution or by transferring the gel to a column for chromatographic elution.

Loading is desirably directly followed by washing with an aqueous solution of the same or similar ionic strength and pH to remove prothrombin and any thrombin which may be present. Advantageously, an acidic pH washing step may additionally be carried out to remove from the chelating gel inter-α-trypsin inhibitor. This protein is recognised as a major unwanted contaminant of Factor IX concentrates prepared by prior art techniques, making up in some cases as much as 30% of the total protein. It has been found, however, that inter-α-trypsin inhibitor can be eluted from $Cu^{2+}$-primed Chelating Sepharose at about pH 4.5–5.5 without appreciable loss of Factor IX from the gel. In order to reduce electrolyte levels in the final product, it is convenient to include at least a final washing step at low ionic strength, e.g. equivalent to 100–200 mM NaCl.

The washing procedure allows for some removal of virus by additional washing steps while the protein is immobilised. Furthermore, the immobilised factors may be treated with a virucide such as a detergent at this stage and the virucide can then be removed by further washing prior to the elution step. It should be noted that the metal chelate material readily binds the protein factors of interest in the presence of detergents and/or solvents used as virucides prior to the initial adsorption according to the invention and can retain these factors when the virucide is removed by washing or indeed, when a virucidal detergent wash is applied prior to elution of the factors. This contrasts with many prior affinity columns used to adsorb such proteins, where detergent tends to affect elution of the proteins.

The clotting factors remaining on the column after removal of Factor II or, indeed, such factors applied to the column in the substantial absence of Factor II, may be eluted by a change of pH and/or use of a displacing agent selected from imidazole and amino acids, desirably at significantly lower ionic strength than the loading buffer solution in order to reduce or avoid the need to remove salts from the resulting enriched fractions. Suitable preferred ionic strengths for such elution are in the range 100–200 mM.

Where elution of desired blood clotting factors depends on a pH gradient, this may be an increasing pH gradient or a decreasing pH gradient and in either case inter-α-trypsin inhibitor may desirably be depleted from the chelating gel prior to collection of a Factor IX-enriched fraction. Thus, in the case of use of an increasing pH gradient for elution, it will be appreciated that the starting pH may be as low as about pH 4.5–5.5 to achieve removal of inter-α-trypsin inhibitor, but this will generally be followed by a substantial step upward in pH for elution of desired blood clotting factors. In particular, for example, it has been found that Factor IX- and Factor X-enriched fractions may be desirably eluted from $Cu^{2+}$-primed Chelating Sepharose in the presence of a non-amino acid or imidazole containing buffer system at relatively low ionic strength, e.g. 100 mM NaCl, by varying the pH linearly from about pH 7.0 to about pH 8.0. In the case of use of a decreasing pH gradient to elute for example from the same type of gel blood clotting factors of a prothrombin complex concentrate, following washing of the gel at above pH 7.0 at high ionic strength e.g. 500 mM NaCl to remove Factor II, elution of Factor X- and Factor IX-enriched fractions substantially free from inter-α-trypsin may desirably be achieved at relatively low ionic strength, e.g. 100 mM NaCl by stepwise decrease of the pH of the elution buffer in the acidic pH range down to about pH 4.0. In this case, the following order of protein elution is observed: Factor X/Factor V (pH about 5–5.6) inter-α-trypsin inhibitor/protein C (pH about 4.6), Factor IX (pH about 4.1).

If it is desired to produce purified or enriched Factor II, this may also preferably be eluted from a metal chelate column at low ionic strength in the absence of amino acids.

Where a displacing agent is employed, the concentration of imidazole or amino acid (in particular, glycine, methionine or glutamic acid) in the eluant is preferably in the range 5 to 70 mM. Suitable amino acids for use in such elution include, for example, alanine, phenylalanine, valine, lysine, glycine, methionine and glutamic acid. The last three named amino acids are particularly preferred for this purpose.

A displacing agent containing eluant is preferably buffered to a pH in the range 4 to 9, more preferably 6 to 8, e.g. about 7. Suitable buffer systems include amino alcohol buffers such as Tris and citrate-phosphate buffer. It is found that Tris enables elution of all the factors at lower concentrations of displacing agent, i.e. imidazole or amino acid.

In general, whichever eluant system is used, the order of elution, which appears to reflect binding affinity, appears to be Factor II/IIa, Factor X, Factor IX/IXa/-Protein C.

In general, elution is preferably carried out in such a way that the eluted protein specific activity (purity and/or potency) is optimised. In general the concentration of the principal factor of interest, e.g. Factor IX, is preferably at least 30 iu/ml.

After elution, the solution may be freeze dried. For inactivation of virus infections, the freeze dried concentrate may be heated at, for example, 80° C. We have found that the purified concentrates according to the invention substantially survive such heating, avoiding significant activation of the respective factors to a greater extent than previous concentrates.

Using the methods of the invention, it has proved possible to prepare for the first time:

(a) Factor IX substantially free of Factor II and inter-α-trypsin inhibitor;
(b) Protein C substantially free from Factors II, IX and X;
(c) Factor X substantially free of Factor II and having specific Factor X activity of at least 13 iu/mg protein; and
(d) Factor VII substantially free from Factor II and having a specific Factor VII activity of greater than one unit per mg protein.

Methods of Testing

The reported incidents of thrombotic episodes following infusion of prior prothrombin complex concentrate has resulted in in vitro and in vivo tests of products for their potential thrombogenic effect. The in vivo tests have been in animals (rabbits, pigs and dogs), using various criteria to asses thrombosis after infusion. In vitro tests are based upon the ability of the concentrate to reduce the clotting time of substrate plasma or fibrinogen. The significance of these tests has not been shown, but great weight is placed upon them in terms of product quality control.

The three main tests are:

NAPTT: Measures level of activated clotting factors in the sample, with an arbitrary lower limit clotting time of 150 seconds. The NAPTT cannot be related conclusively to the concentration of any particular activated clotting factor but indicates the presence of F.IXa and F.Xa.

FCT: Measures the time taken for a fibrinogen solution to clot in the presence of test material. This is a direct measure of thrombin (the penultimate protein in the blood clotting "cascade"). The lower limit clotting time is three hours, which corresponds to $5 \times 10^{-3}$ iu/ml or 2 ng/ml of thrombin.

TGt 50: Measures the time taken to generate a known amount of thrombin. It is a measure of the activation of clotting factors which operate earlier in the process.

The following Examples are given by way of illustration only.

Tests Used in the Examples for Quantification of Proteins

Both functional biological activity and antigenic activity were used to quantitate the proteins of interest.

Biological activity of Factors II, IX and X was measured by established clotting assays. Unitage of clotting activity (:C) was defined using a Working Standard 87/532 which had been calibrated against the 1st International Standard for Factors II, IX and X Concentrates, code 84/681.

Biological activity of Factor VII was measured by established clotting assay or by chromogenic assay using a synthetic substrate. In both cases, unitage was assigned using an in-house Factor VII concentrate working standard which had been calibrated against a human plasma pool of greater than thirty donors, defined as having a Factor VII activity of 1.0 F.VII:C u/ml.

All antigen activities (:Ag) for Factors II, V, IX and X, Protein C and Inter-α-Trypsin Inhibitor were measured by Immune Electrophoresis (Laurell's Rocket method) using Normal Pooled Plasma as the standard. In each case, the standard had been assigned a potency of 1.0 unit per ml and sample activities were expressed as plasma equivalent units per ml.

In the present specification, clotting activity or "Factor -:C" is given in terms of international units per ml or iu/ml. Antigen activity or "Factor -:Ag" is given as units per ml (u/ml) or plasma equivalent units per ml (p.e.u/ml).

As the clotting and antigen activities are measures of different aspects of the protein chemistry, the international unit of clotting activity is not the same as the plasma equivalent unit. Typically, the ratio of iu: p.e.u. for Factor II, Factor IX and Factor X in partially purified protein concentrates is 0.86, 0.6 and 0.63 respectively.

Example 1

Preparation of Prothrombin from Prothrombin Complex Concentrate (PCC)

Chelating Sepharose was primed with copper ions by passing copper sulphate solution through it. The gel was then washed with citrate-phosphate buffer containing 500 mM NaCl at pH 7.0. PCC containing 500M NaCl was applied to the column at a loading of 100–200 Factor IX iu per ml gel. The protein eluate was monitored and the breakthrough protein collected. This. contained prothrombin at potencies of 5–25 iu/ml with a specific activity of 5 iu/mg protein. This material was at least 70% prothrombin.

Example 2

Effect of ionic strength on binding of Factors II, IX, X and Protein C to copper-chelate gel.

PCC was dialysed against citrate-phosphate buffer pH 7.0 containing 100, 250,500 or 1000 mM NaCl. This was then loaded on to a $Cu^{2+}$-primed Chelating Sepharose column, which had been washed with the same ionic strength buffer. After loading at 430 units per ml of gel, the column was further washed with the same buffer and the eluted unbound protein assayed for Factors II, IX, X and Protein C. Table I below shows the results.

TABLE 1

| Adsorption [NaCl] (mM) | Unbound units per ml of gel | | | |
|---|---|---|---|---|
| | F.II | F.IX | F.X | PC |
| 100 | 162 | 64 | 82 | 14 |
| 250 | 155 | 64 | 87 | 13 |
| 500 | 138 | 49 | 74 | 10 |
| 1000 | 95 | 35 | 55 | 7 |

Maximum differential binding of Factor IX over Factor II was observed at 500 mM NaCl

Example 3

Effect of adsorption pH on binding of Factors II, IX and X to copper-chelate gel.

Chelating Sepharose was first primed with copper ions and then washed with a citrate-phosphate buffer system containing 500 mM NaCl with pH adjusted to the indicated level. PCC, containing 500 mM NaCl, was titrated to the same-pH and then loaded on to the gel at about 300 Factor IX units per ml of gel. The column was further washed with the same buffer and the breakthrough/unbound protein collected and measured for Factors II, IX and X. Table II below shows the results.

TABLE II

| Adsorption pH | Unbound units per ml of gel | | |
|---|---|---|---|
| | F.II | F.IX | F.X |
| 5.5 | 231 | 69 | 121 |
| 6.0 | 227 | 64 | 93 |
| 6.5 | 189 | 64 | 74 |
| 7.0 | 234 | 71 | 69 |
| 7.5 | 285 | 43 | 75 |
| 8.2 | 328 | 59 | 155 |

Optimum binding of Factor II was achieved between pH 6.0–7.0.

Optimum binding of Factor IX was achieved above pH 7.0.

Optimum binding of Factor X was achieved between pH 6.5 and pH 7.5.

Adsorption pH can therefore be used to optimise the binding of a preferred clotting factor to the gel.

Example 4

Preparation of a concentrate of Factor X and Factor IX with Reduced Prothrombin

A Chelating Sepharose column was prepared and loaded as in Example 1. After application of the PCC, the column was washed with citratephosphate buffer containing 500 mM NaCl at pH 7.0. The ionic strength was then reduced by washing with citrate-phosphate buffer containing 100 mM NaCl The Factor X fraction was then eluted with citrate-phosphate buffer containing 100 mM NaCl and 5 mM glycine. This contained Factor X at 15–40 Factor X iu/ml and less than 0.01 unit prothrombin per unit of Factor X. The Factor X specific activity was 13 iu/mg protein and was therefore 7% pure. This fraction also contained Factor IX in approximately equimolar amounts (1 iu Factor IX per unit Factor X).

Example 5 preparation of Factor X with reduced Prothrombin and Factor IX

A Chelating Sepharose column was primed and loaded as described in Example 1. After application of the sample, the column was washed with citratephosphate buffer containing 500 mM NaCl at pH 7.0. The Factor X was then eluted with citrate-phosphate buffer at pH 7.0 containing 500 mM NaCl and 5 mM glycine. This material contained 15–30 Factor X iu/ml with a specific activity of 14 iu/mg protein. This material differed from that obtained in Example 4 by having higher prothrombin activity and lower Factor IX activity. Here, 0.25 iu/unit Factor X was obtained for both prothrombin and Factor IX. Therefore, the prothrombin still constituted about 40–50% by weight of the total protein.

Example 6

Preparation of a concentrate of Factor IX and Factor X with reduced Prothrombin

A Chelating Sepharose column was primed and loaded as described in Example 1. It was then washed sequentially with citrate-phosphate buffer containing first 500 mM and then 100 mM NaCl at pH 7.0. Both Factor IX and Factor X were then eluted with Tris-glycine buffer containing 100 mM NaCl, at potencies of 30 iu/ml. Prothrombin was reduced to 0.03 iu per unit of Factor IX or Factor X.

Example 7

Preparation of a concentrate of Factor IX and Protein C with reduced Prothrombin and Factor X A Chelating Sepharose column was prepared and washed as described in Example 4. After elution of protein in 5 mM glycine, Tris-glycine buffer was used to elute Factor IX. It was found that Tris was suitably in the range 10–30 mM, glycine in the range 40–70 and NaCl 100 mM. This eluted Factor IX at potencies of 30–50 iu/ml. Prothrombin was undetectable and Factor X showed less than 0.01 unit per unit of Factor IX (less than 0.05% by weight). Protein C was also eluted at concentrations of 25–40 plasma equivalent units per ml.

Example 8

Separation of Protein C from Prothrombin and Factor X

Purification of Protein C is complicated by co-elution of prothrombin and Factor X in conventional chromatographic systems such as heparin-Sepharose or Dextran-Sulphate-Sepharose. However, in these systems, Factor IX contamination is minimal due to tighter binding of that protein. The metal chelate system described here can therefore be used as a step in the purification of Protein C.

The preparation and washing of a Chelating Sepharose column was as described in Example 7. As protein binding is concentration dependent, loading was as high as possible, up to 160 Factor X iu per ml gel or 240 prothrombin iu per ml of gel. The column was then washed and eluted as described in Example 7, with the Protein C eluting with the final Tris-glycine buffer eluant, separated from prothrombin and Factor X contaminants.

Example 9

Effect of adsorption contact time on binding and recovery of Factor II, Factor IX, Factor X and Protein C from $Cu^{2+}$-primed Chelating Sepharose.

Chelating Sepharose was packed into columns, primed with copper ions and then washed with citrate-phosphate buffer pH 7.0 containing 500 mM NaCl PCC, containing 500 mM NaCl, was loaded on to each column at a controlled flow rate so that the contact time with the gel could be varied in different columns. The columns were loaded at 430 Factor IX units per ml gel, washed with the 500 mM NaCl buffer, then with 100 mM NaCl buffer and then with 10mM Tris, 70 mM glycine, 100 mM NaCl buffer pH 7.0. The breakthrough and the Tris-glycine eluates were measured for Factor II, Factor IX, Factor X and Protein C. The results are shown in Table III below.

TABLE III

| Contact Time | Unbound units per ml gel | | | | Eluted units per ml gel | | | |
|---|---|---|---|---|---|---|---|---|
| (mins) | F.II | F.IX | F.X | PC | F.II | F.IX | F.X | PC |
| 10 | 172 | 156 | 153 | 27 | 91 | 231 | 135 | 66 |
| 20 | 198 | 151 | 126 | 26 | 64 | 216 | 91 | 68 |
| 40 | 189 | 63 | 66 | 13 | 39 | 242 | 160 | 78 |
| 70 | 210 | 57 | 57 | 11 | 37 | 227 | 142 | 77 |
| 110 | 247 | 72 | 105 | 18 | 23 | 266 | 126 | 93 |

Binding of protein to the gel is therefore dependent on contact time. This can be optimised for Factors IX, X and Protein C at contact times of forty minutes or greater. Increased contact time results in less Factor II binding to the gel.

Example 10

Effect of loading challenge on the binding and recovery of Factor II, Factor IX, Factor X and Protein C with $Cu^{2+}$-primed Chelating Sepharose.

Chelating Sepharose was packed into several columns, primed with copper ions and washed with citrate phosphate buffer pH 7.0 containing 500 mM NaCl PCC, containing 500 mM NaCl, was loaded on the columns in different amounts, the contact time for each column being maintained at 40 minutes by varying the flow rate through the column. The columns were then washed with buffers as described in Example 6. The results are shown in Table IV below.

TABLE IV

| Loading F.IX:Ag units | Unbound units per ml gel | | | | Eluted units per ml gel | | | |
|---|---|---|---|---|---|---|---|---|
| per ml gel | F.II | F.IX | F.X | PC | F.II | F.IX | F.X | PC |
| 43 | 6 | 0 | 0 | 0 | 13 | 30 | 23 | 9 |
| 88 | 13 | 1 | 2 | 0 | 23 | 76 | 46 | 19 |
| 173 | 54 | 15 | 18 | 2 | 42 | 112 | 85 | 37 |
| 258 | 115 | 49 | 43 | 11 | 45 | 165 | 100 | 52 |
| 344 | 185 | 55 | 52 | 11 | 31 | 186 | 115 | 62 |
| 430 | 189 | 63 | 66 | 13 | 39 | 242 | 160 | 78 |
| 513 | 305 | 175 | 128 | 42 | 26 | 256 | 136 | 79 |

Increased loading displaces Factor II preferentially. Loading challenge can be used to enhance the binding and recovery of one particular protein relative to the others. Improved separation of Factor IX from Factor II was achieved at loadings of 258–430 F. IX:Ag units per ml of gel (equivalent to approximately 150–250 F.IX:C iu per ml of gel).

Example 11

Effect of Factor IX concentration on binding and recovery of Factor II, Factor IX, Factor X and Protein C with $Cu^{2+}$-primed Chelating Sepharose.

Chelating Sepharose was primed with copper ions and washed as described in previous examples. PCC containing 500 mM NaCl was diluted in citrate-phosphate buffer pH 7.0 containing 500 mM NaCl Columns were loaded at different dilutions and washed with buffers as described in Example 6. Total loading challenge (approx. 250 units per ml of gel) and contact times were kept constant. The results are shown in Table V below.

TABLE V

| Loading potency Unbound units per F.IX:Ag | Eluted units per | | | | | | | |
|---|---|---|---|---|---|---|---|---|
| | ml gel | | | | ml gel | | | |
| u/ml gel | F.II | F.IX | F.X | PC | F.II | F.IX | F.X | PC |
| 173 | 180 | 75 | 140 | 17 | 15 | 200 | 142 | 70 |
| 86 | 195 | 80 | 145 | 20 | 10 | 170 | 125 | 65 |
| 43 | 245 | 140 | 185 | 35 | 7 | 185 | 115 | 55 |

Higher concentrations of the loaded material are preferred for binding to the chelate to occur.

Example 12

Effect of chelating gel on Factor IX binding and recovery

Equal volumes of five chelating gel types were packed into five columns, primed with $Cu^{2+}$ ions and washed with citrate-phosphate buffer pH 7.0 containing 500 mM NaCl. PCC, adjusted to contain 500 ml NaCl was loaded in equal amounts on to each column, followed by washing sequentially with the same buffer, buffer containing 100 mM NaCl and then elution with 10 mM Tris, 70 mM glycine buffer pH 7.0. Factor IX was measured in the breakthrough, wash and eluate fractions.

Gel types used were:
1. Chelating Sepharose comprising iminodiacetic acid attached to Sepharose by a 12 atom (10 carbon) spacer molecule [Pharmacia].
2. As for 1 but with additional cross-linking for Fast Flow Sepharose.
3. Agarose carrying iminodiacetic acid attached by a 12 atom (10 carbon) spacer molecule [Sigma]
4. Iminodiacetic acid directly attached to a styrene-divinyl benzene cross-linked polymer [Chelex 100, BioRad].
5. As 4 but with a coarse mesh, non-cross-linked matrix [Chelex 20, BioRad].

Table VI below shows the results.

TABLE VI

| Gel Type | Factor IX % of loaded | | |
|---|---|---|---|
| | Breakthrough | Wash | Eluate |
| 1 | 8.9 | 4.6 | 60.2 |
| 2 | 14.7 | 13.3 | 43.4 |
| 3 | 12.1 | 60.2 | 20.9 |
| 4 | 76.0 | 0.2 | 0.2 |
| 5 | 93.0 | 2.1 | 0.4 |

Factor IX binding to $Cu^+$-primed iminodiacetic groups is increased by provision of a spacer molecule between the matrix and the chelating group and by the use of non-cross-linked Chelating Sepharose. Example 13

Preparation of Factor IX using $Cu^{2+}$-primed Chelating Sepharose in a batch adsorption.

Chelating Sepharose was washed with water, then suspended in a copper sulphate solution (5mg/ml) and mixed for 20–30 minutes. The $Cu^{2+}$-primed gel was recovered from the mixture by centrifugation and washed extensively with citrate-phosphate buffer pH 7.0 containing 500 mM NaCl. The gel was recovered as above, resuspended in a solution of PCC containing 500 mM NaCl and mixed for 20–30 minutes. The ratio of PCC to gel was approximately 150 Factor IX:C units per ml of gel. The gel was recovered by centrifugation or gravity settling and the supernatant removed.

Sequence washes with citrate-phosphate buffer pH 7.0 containing 500 mM NaCl then 100 mM NaCl removed weakly-bound protein and reduced the ionic strength. Factor X could then be removed by washing with 10 mM Tris, 5 mM glycine, 100 mM Nacl pH 7.0. Factor IX was subsequently eluted by washing the gel with 10 mM Tris, 70 mM glycine, 100 mM NaCl pH 7.0.

Example 14

Recovery of Factor IX from $Cu^{2+}$-primed Chelating Sepharose using different amino acid elution buffers Columns of Chelating Sepharose were primed with $Cu^{2+}$ ions and washed as described in previous examples. PCC (containing 500 mM NaCl) was loaded on to each column, followed by washing with citrate-phosphate buffer pH 7.0. Factor I was recovered by eluting with 10 mM Tris, pH 7.0, containing at 70 mM an amino acid selected from (a) non-polar amino acids e.g. alanine, valine, phenylalanine, methionine), (b) polar uncharged amino acids (e.g. glycine, serine, tyrosine, glutamine), (c) polar negatively charged amino acids (e.g. glutamic acid) or (d) polar positively charged amino acids (e.g. lysine, arginine). Methionine, glycine and glutamic Acid were found to be particularly advantageous, these giving Factor IX yields of greater than 80% and Factor IX specific activities of greater than 5 i u/mg.

Example 15

Elution of Factor X and Factor IX from Chelating Sepharose using Methionine

A column of $C^{2+}$-primed Chelating Sepharose was washed with citrate phosphate buffer pH 7.0 containing 500 mM NaCl PCC was applied to the column, which was then washed with the same buffer before reducing the ionic strength by washing with a buffer containing 100 mM NaCl Factor X was then eluted with Tris buffer pH 7.0 containing 2 mM-5 mM methionine. The Factor X potency was greater than 15 u/ml and the specific activity was approximately 30 units/mg. Factor IX was reduced in the Factor X fraction to about 0.5 unit Factor IX per unit Factor X and prothrombin was present at less than 0.1 unit per unit Factor X.

Factor IX was found to be eluted by washing with Tris buffer containing 10-15 mM methionine. The Factor IX potency was greater than 15 u/ml and it had a specific activity of approximately 20 units/mg. Prothrombin was undetectable in the Factor IX fraction and Factor X was present at less than 0.1 Factor X unit per unit of Factor IX.

Example 16

Elution of Factor X and Factor IX from Chelating Sepharose using Glutamic Acid

A $Cu^{2+}$-primed Chelating Sepharose column was prepared, washed and loaded with PCC and washed as described for methionine elution (Example 15).

Factor X was eluted with 10 mM Tris buffer containing 5 mM-10 mM glutamic acid. The Factor X had a specific activity of 16-22 units/mg.

Factor IX, with a specific activity of approximately 15 u/mg was then eluted by raising the glutamic acid concentration in the eluting buffer to 40 mM.

Example 17

Preparation of Factor IX and Factor X using an increasing DH gradient to elute from Chelating Sepharose A column of Chelating Sepharose was primed with $Cu^{2+}$ ions and washed with buffer at pH 7.0 containing 500 mM NaCl PCC containing 500 mM NaCl was loaded on to the column, which was then washed with buffer. Ionic strength was reduced to 100 mM NaCl using low salt buffer at pH 7.0. Some Factor X was eluted by this buffer with a specific activity of 10.5 u/mg.

The column was progressively eluted by a pH gradient from pH 7.0 to pH 8.5. Factor IX and Factor X were eluted between pH 7.1 and pH 7.9 with specific activities of 27 u/mg and 6 u/mg respectively.

Example 18

Preparation of Factors IX, X and Protein C using pH and glycine to elute

A column of Chelating Sepharose was primed with $Cu^{2+}$ ions and washed with citrate-phosphate buffer, pH 7.5. PCC containing 500 mM NaCl was adjusted to pH 7.5 and loaded on to the column, which was washed with buffer. Ionic strength was then reduced by washing with citrate-phosphate buffer pH 7.5 containing 100 mM NaCl. This eluted Factor X with a specific activity of 18 u/mg in a mixture with Factor IX, which had a specific activity of 9 u/rag. A combined Protein C (15 u/ml; 6.5 units per mg protein) and Factor IX (12 u/ml; 5 units per mg protein) fraction was then collected by washing with 10 mM Tris, 5 mM glycine, 100 mM NaCl buffer, pH 8.0.

Example 19

Elution of protein components from Chelating Sepharose using a decreasing pH gradient A column of Chelating Sepharose was primed with $Cu^{2+}$ ions and washed with citrate-phosphate buffer pH 7.5 containing 500 mM NaCl. PCC was then applied after adjustment of pH to 7.5 and NaCl to 500 mM. This was followed by use of the above buffer as a wash to remove Factor II. 30% of the Factor V is the starting material was also removed in this wash. Ionic strength was then reduced by washing with buffer containing 100 mM NaCl. This also removed Factor X at a specific activity of about 15 units per mg protein. Using citrate-phosphate buffers, a pH gradient was generated during washing of the column from pH 7.5 to pH 4.0. It was found that fractions could be collected which were rich in selected proteins. Thus, for example, at about pH 5.5, Factor X was further removed while between pH 5 and pH 5.6, a further 40% of the bound Factor V was removed from the column at about five plasma equivalent units per ml.

In this pH range, Inter-α-Trypsin Inhibitor also started to elute, as did Protein C. As the buffer pH fell to pH 4.6, Inter-α-Trypsin Inhibitor and Protein C elution continued with specific activities of 3.0 and 4.6 plasma equivalent units per mg protein respectively. Only small amounts of Factor IX were eluted during these segments of the descending pH gradient.

When the pH was then reduced further, for example to pH 4.1, Factor IX was eluted at potencies greater than 40 units per ml and specific activities of greater than 30 units per mg protein. This fraction contained no detectable Factor II or Factor X. Protein C was present at about 0.01 units per unit of Factor IX, Factor V was present at 0.06 units per unit of Factor IX and Inter-α-Trypsin Inhibitor was present at 0.03 units per unit of Factor IX. In terms of their contamination of one unit of Factor IX, this represents a reduction in Protein C, Factor V and Inter-α-Trypsin Inhibitor of 95%, 63% and 90% respectively over the starting material (PCC).

Example 20

Use of pH and amino acid to separate protein components from Chelating Sepharose A column of Chelating Sepharose was primed with $Cu^{2+}$ ions and washed with citrate-phosphate buffer pH 7.5 containing 500 mM NaCl PCC, adjusted to contain 500 mM NaCl and with a pH of 7.5, was loaded on to the column, which was then washed with the buffer described above. A further wash with citrate-phosphate buffer pH 7.5 containing 100 mM NaCl reduced the ionic strength and removed Factor X, which could be collected at a potency of at least 6 u/ml and a specific activity of at least 15 units per mg protein. The pH was then reduced by washing with a third buffer, typically citrate-phosphate pH 4.5 containing 100 mM NaCl. This removed at least 55% of the remaining bound Inter-α-Trypsin Inhibitor and 24% of the remaining bound Protein C, but only 5% of the bound Factor IX. The column was then re-equilibrated in a buffer having a pH and salt concentration suitable for Factor IX elution, typically pH 7.0 100 mM NaCl. The Factor IX was then eluted with an amino acid eluant buffer, e.g. glycine in Tris buffer containing 100 mM NaCl as described in previous examples. This yielded Factor IX at 200 u/ml with a specific activity of greater than 50 units per mg protein. Protein C was also present with a specific activity of 20 plasma equivalent units per mg of protein.

Compared to the starting PCC material, the Factor IX fraction contained significantly reduced amounts of contaminating proteins. Factor II, Factor X, Factor V and Inter-s-Trypsin Inhibitor were present per unit of Factor IX at levels of 0.0005, 0.005, 0.002 and 0.04 units respectively. This compared with values of 1.0, 1.0, 0.2 and 0.4 respectively in the PCC starting material.

Example 21

Preparation of Factor VII on $Cu^{2+}$-primer Chelating Sepharose

A column of Chelating Sepharose was charged with $Cu^{2+}$ ions, then washed with citrate-phosphate buffer pH 7.0, containing 500 mM NaCl. Factor VII concentrate, prepared by elution of DEAE-Sepharose adsorbed with cryosupernatant or Factor IX-depleted supernatant, was adjusted to contain 500 mM NaCl and loaded on to the column at 50–150 Factor VII units per ml of gel. After washing with the above buffer, the ionic strength was reduced by washing with citrate-phosphate buffer pH 7.0, containing 100 mM NaCl. The Factor VII was recovered with a specific activity of greater than one unit per mg by washing the column with 10 mM Tris, 60 mM glycine at pH 7.0 containing 100 mM NaCl.

Example 22

Detergent treatment of blood clotting factors while adsorbed on Chelating Sepharose Chelating Sepharose was charged with $Cu^{2+}$ ions washed and then loaded as described in Example 1. The column was then washed with citrate-phosphate buffer at pH 7.0 containing 500 mM NaCl. The column was then washed with at least four bed volumes of the same buffer containing 1% by weight of sodium docecyl sulphate to solubilise lipid components bound to the gel. Next, the detergent was washed from the gel with citrate-phosphate buffer containing 100 mM NaCl. This stage also served to reduce the ionic strength by desalting. Factor IX was then eluted from the gel with glycine in Tris buffer as described in Example 7. Using the same procedure, the sodium dodecyl sulphate may be replaced by the same weight of cholic acid or polyoxyethylene (20) mono-oleate (Tween 80).

Example 23

Freeze-driving and subsequent heat-treatment of the final fractions of Examples I and 4–7

Eluates of the above specified Examples were freeze-dried without loss of activity, and then heated at 80° C. for 72 hours to reduce potential viral infectivity. Unlike existing PCC, no thrombin generation was observed upon heating. Factors II, IX and X showed different stabilities to heating in different media. If eluates were diluted into citrate and water, heating yields of 65–90% of the unheated activity were obtained. Dilution into Tris resulted in much greater loss of activity, which was greater for Factor X than for prothrombin and greater for Factor IX than for Factor X. This general effect can be used to advantage as described below in Examples 24 and 25.

Example 24

Reduced Factor IX activity in a concentrate of Factor X

Example 4 and Example 6 above describe preparation of a Factor X concentrate with Factor IX also present. The Factor IX activity can be preferentially reduced by dilution of the relevant Factor X fractions into 50 mM Tris buffer pH 7.0 prior to freeze-drying. Alternatively, to avoid dilution of the eluate Factor X potency, the Tris in the eluting buffer can be increased to 50mM so that the Factor X is eluted in its formulation buffer. After freeze-drying, this material can be heated at 80° C. for 72 hours. Factor IX activity will be reduced more than Factor X so that the product may be used with greater specificity as a Factor X concentrate.

Example 25

Heat-treatment of high purity Factor IX concentrate

In order to attain the maximum possible yields of Factor IX activity after heating, the Factor IX eluate described in Example 7 was diluted to the desired final potency in citrate or citrate-phosphate buffers or in water, freeze-dried then heat-treated at 80° C. for 72 hours. The eluting buffer contained Tris, but the effect of this was minimised by selection of fractions with sufficiently high Factor IX potency to permit the effective diluting out of the Tris component into the final buffer. Alternatively the formulation of the eluting buffer may be modified to allow direct freeze-drying of the undiluted eluate.

I claim:

1. A method for producing a composition enriched in a vitamin K-dependent blood clotting factor from a non-enriched composition containing at least one such factor, which comprises contacting said non-enriched composition to adsorb said non-enriched composition onto a copper chelate adsorbent comprising an inert support carrying $Cu^{2+}$ ions chelated with iminiodiacetic acid groups attached to the support via spacer chains, said spacer chains being carbohydrate chains or linear hydrocarbon chains and optionally substituted with hydroxyl groups and having up to two oxygen atoms in the chain, said spacer chains having up to 16 atoms in the chain between the inert support and the iminodiacetic acid group, and eluting to recover an adsorbed fraction from said copper chelate adsorbed which is enriched in said vitamin K-dependent factor.

2. The method according to claim 1, wherein said non-enriched composition is a prothrombin complex concentrate.

3. The method according to claim 1, wherein said non-enriched composition is adsorbed onto said chelate in the presence of an aqueous solution containing 0.4 to 1.0M NaCl.

4. The method according to claim 3, wherein said solution contains 0.5M NaCl.

5. The method according to claim 1, wherein a prothrombin complex concentrate is adsorbed onto an agarose support over a period of greater than 20 minutes to achieve a Factor IX loading of 100–450 F.IX:AG units per ml. of gel.

6. The method according to claim 1 wherein adsorption of said non-enriched composition is followed by washing of the support to remove bound Factor II prior to elution of any fraction enriched in a vitamin K-dependent blood clotting factor.

7. The method according to claim 1, wherein adsorption of said mixture is followed at least one washing step wherein the one washing step or a last washing step is carried out with a bufffer solution containing 100–200 mM NaCl.

8. The method according to claim 1, wherein elution of one or more desired vitamin K-dependent blood clotting factors adsorbed onto said support is achieved by means of a pH gradient.

9. The method according to claim 1, wherein elution of one or more desired vitamin K-dependent blood clotting factors adsorbed onto said support is achieved by means of a buffer solution containing an amino acid selected from the group consisting of glycine, methionine and glutamic acid.

10. The method according to claim 1 further comprising an elution group employing an acidic pH solution to specifically remove bound inter-α-trypsin inhibitor from the support.

11. The method according to claim 10 wherein said elution step is followed by collection of a Factor IX-enriched fraction essentially free of said inhibitor and Factor II.

12. The method according to claim 1, wherein at least one of a Factor X-enriched fraction, a Factor VII-enriched fraction and a Protein C-enriched fraction is obtained, essentially free of Factor II.

13. The method according to claim 1, wherein said adsorbing and eluting are carried out by column chromatography.

14. The method according to claim 1, wherein said mixture is adsorbed onto said chelate in a buffer solution of $pH \geq 6.0$.

15. The method of claim 14, wherein said buffer solution has a pH value of $6.0 \leq pH \leq 7.5$.

16. The method according to claim 1, wherein said mixture contains at least two different vitamin K-dependent blood clotting factors.

17. The method according to claim 1, wherein said mixture is adsorbed onto said chelate in the presence of an aqueous solution containing electrolytes providing a total salt concentration of 0.4 to 1.0M, wherein one of said electroytes is NaCl.

18. The method according to claim 1, wherein said solution contains electrolytes providing a final salt concentration of 0.5M, wherein one of said electrolytes is NaCl.

19. The method according to claim 1, wherein said mixture is adsorbed onto said chelate in the presence of a buffer solution of $pH \geq 6.0$.

20. The method according to claim 1, wherein adsorption of said mixture is followed by at least one washing step wherein the one step or a last washing step is carried out with a buffer solution containing electrolytes providing a final salt concentration of 100–200 mM, wherein one of said electrolytes is NaCl.

* * * * *